(12) United States Patent
Balogh, II

(10) Patent No.: US 6,907,877 B2
(45) Date of Patent: Jun. 21, 2005

(54) SUSPENDED INHALER RETAINER

(76) Inventor: John Ernest Balogh, II, 5301 31st Ave., South, Gulfport, FL (US) 33707

( * ) Notice: Subject to any disclaimer, the term of this patent is extended or adjusted under 35 U.S.C. 154(b) by 0 days.

(21) Appl. No.: 10/348,768

(22) Filed: Jan. 21, 2003

(65) Prior Publication Data

US 2003/0141325 A1 Jul. 31, 2003

Related U.S. Application Data

(60) Provisional application No. 60/349,474, filed on Jan. 18, 2002.

(51) Int. Cl.[7] ............................................. A61M 15/00
(52) U.S. Cl. .............................. 128/200.24; 128/200.23
(58) Field of Search ....................... 128/200.24, 200.23, 128/205.22; 24/3.4, 115 H, 265 H; 224/148.6, 219–221, 251

(56) References Cited

U.S. PATENT DOCUMENTS

| | | | | |
|---|---|---|---|---|
| 222,899 A | * | 12/1879 | Hartman | 224/251 |
| 534,946 A | * | 2/1895 | Bates | 224/220 |
| 860,189 A | * | 7/1907 | Chartfield | 24/115 H |
| 1,200,012 A | * | 10/1916 | Oldham | 24/136 L |
| 1,455,879 A | * | 5/1923 | Gronlund | 24/3.13 |
| 1,509,781 A | * | 9/1924 | Roth | 119/795 |
| 2,233,157 A | * | 2/1941 | Cahn et al. | 206/361 |
| 2,572,889 A | * | 10/1951 | Strykower | 224/258 |
| 2,644,623 A | * | 7/1953 | White | 224/148.5 |
| 2,781,959 A | * | 2/1957 | Loveland | 224/572 |
| 2,840,873 A | * | 7/1958 | Meier | 403/17 |
| 2,907,539 A | * | 10/1959 | Vardan | 248/104 |
| 2,911,694 A | * | 11/1959 | Seron | 24/371 |
| 2,947,456 A | * | 8/1960 | Seron | 224/258 |
| 3,144,230 A | * | 8/1964 | Brooks | 248/102 |
| 3,186,611 A | * | 6/1965 | Sonderman | 224/605 |
| 3,197,099 A | * | 7/1965 | Doba | 224/148.4 |
| 3,266,464 A | * | 8/1966 | Davis | 119/756 |
| D208,318 S | * | 8/1967 | Kirsh | D44/10 |
| 3,369,723 A | * | 2/1968 | Saari et al. | 224/148.6 |
| 3,397,026 A | * | 8/1968 | Spina | 351/157 |
| 3,737,649 A | * | 6/1973 | Nelson et al. | 362/102 |
| 4,176,773 A | * | 12/1979 | Wilkinson | 224/604 |
| 4,220,302 A | * | 9/1980 | Hampton et al. | 248/102 |
| 4,330,073 A | * | 5/1982 | Clark | 224/223 |
| 4,577,374 A | * | 3/1986 | Lii | 24/165 |
| 4,658,814 A | * | 4/1987 | Anderson | 128/207.17 |
| 4,700,408 A | * | 10/1987 | Winger | 24/3.4 |
| 4,993,611 A | * | 2/1991 | Longo | 224/148.4 |
| 5,007,566 A | * | 4/1991 | Fick | 224/414 |
| 5,027,477 A | * | 7/1991 | Seron | 24/3.4 |
| 5,092,018 A | * | 3/1992 | Seron | 24/3.4 |
| 5,127,137 A | * | 7/1992 | Krauss | 24/265 R |
| 5,136,756 A | * | 8/1992 | Krauss | 24/265 H |
| 5,244,135 A | * | 9/1993 | Nelson | 224/604 |
| 5,274,887 A | * | 1/1994 | Fudaki | 24/265 H |
| 5,277,733 A | * | 1/1994 | Effertz | 156/215 |

(Continued)

*Primary Examiner*—Aaron J. Lewis
(74) *Attorney, Agent, or Firm*—Charles H. Thomas

(57) ABSTRACT

A medication inhaler is provided with a lanyard that is formed into a wearer neck encircling loop. A wearer is thereby able to carry the medication inhaler about his or her neck so that it is readily at hand in the event of an asthmatic or allergic attack. The lanyard may be looped directly about the inhaler and secured thereto by a cinch, slide, slipknot, or some other means. Alternatively, the lanyard may be connected to a socket designed to receive and capture the inhaler. A releasable coupling is provided with a pair of mutually engageable and separable coupling elements. At least one of the coupling elements is connected to the lanyard so that if the inhaler becomes caught or snagged on some object, the coupling members will separate to prevent injury to the user. Preferably the lanyard is formed with a pair of opposing ends at which the mutually engageable coupling members are located. In this way the coupling members will separate if either the lanyard or the inhaler becomes caught on some object.

4 Claims, 6 Drawing Sheets

U.S. PATENT DOCUMENTS

| | | | | |
|---|---|---|---|---|
| 5,381,922 A | * | 1/1995 | Gladman et al. | 220/481 |
| 5,397,039 A | * | 3/1995 | Parcelles | 224/148.5 |
| 5,641,103 A | * | 6/1997 | Potik et al. | 224/251 |
| 5,664,712 A | * | 9/1997 | Smrt | 224/250 |
| 5,730,118 A | * | 3/1998 | Hermanson | 128/200.14 |
| 5,772,090 A | * | 6/1998 | Rodriguez | 224/251 |
| 5,779,122 A | * | 7/1998 | Martinelli | 224/683 |
| 5,833,093 A | * | 11/1998 | Honaker et al. | 222/175 |
| 5,839,631 A | * | 11/1998 | Hebert et al. | 224/251 |
| 5,855,307 A | * | 1/1999 | Biddick et al. | 224/267 |
| 5,875,945 A | * | 3/1999 | Roach | 224/217 |
| 6,032,841 A | * | 3/2000 | Johnson | 224/463 |
| 6,036,066 A | * | 3/2000 | Giacona, III | 224/148.6 |
| 6,109,490 A | * | 8/2000 | Caluori | 224/220 |
| 6,164,275 A | * | 12/2000 | Van Iderstine | 128/200.14 |
| 6,176,403 B1 | * | 1/2001 | Svare et al. | 224/251 |
| 6,216,319 B1 | * | 4/2001 | Elkins | 24/3.2 |
| 6,321,958 B1 | * | 11/2001 | Erdmann | 224/236 |
| 6,357,586 B2 | * | 3/2002 | Pratt et al. | 206/315.9 |
| 6,360,929 B1 | * | 3/2002 | McCarthy | 224/251 |
| 6,539,588 B1 | * | 4/2003 | Brosofsky et al. | 24/3.4 |
| 6,557,737 B1 | * | 5/2003 | Hanson | 224/148.6 |
| 6,685,068 B1 | * | 2/2004 | Thompson et al. | 224/251 |

\* cited by examiner

FIG. 2
FIG. 2A
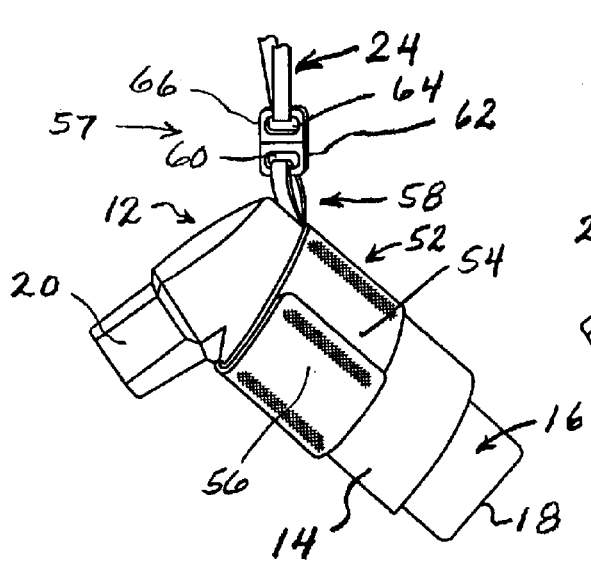
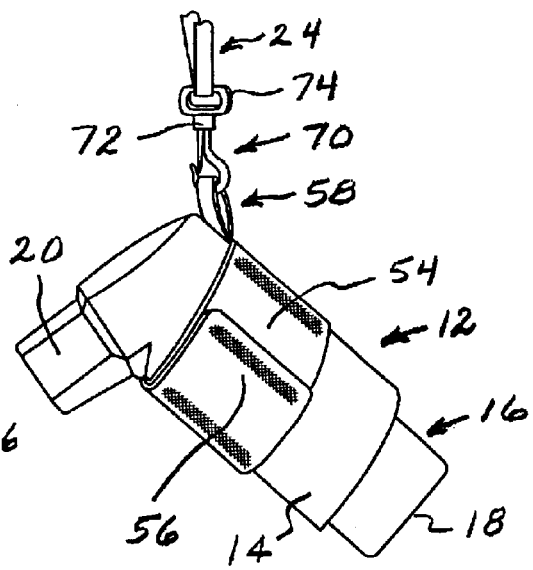
FIG. 3
FIG. 3A
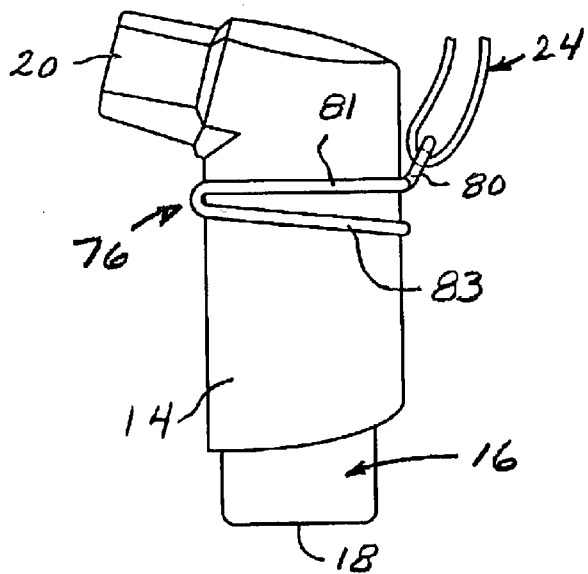
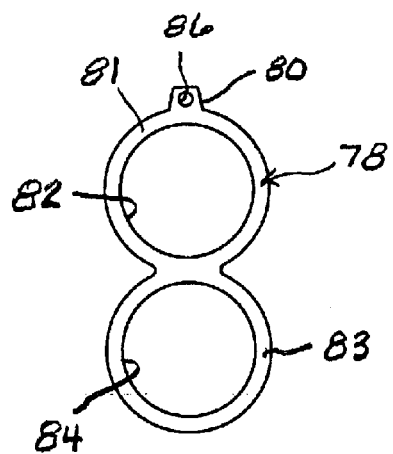

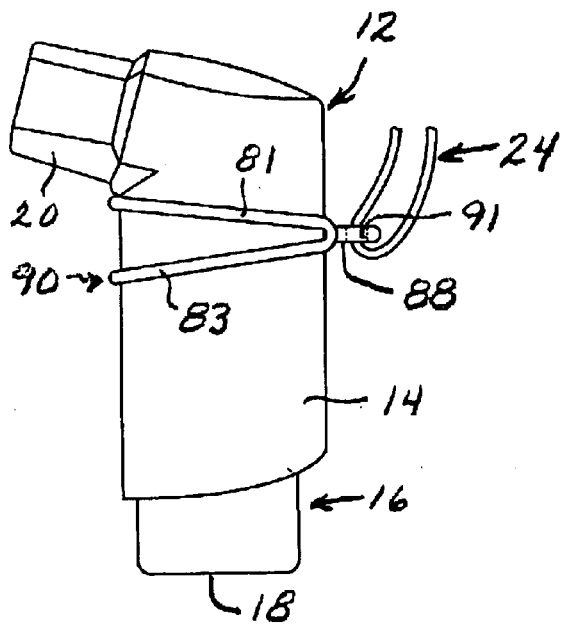
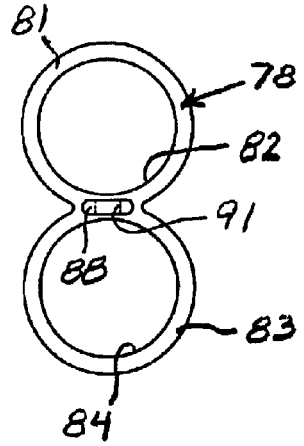
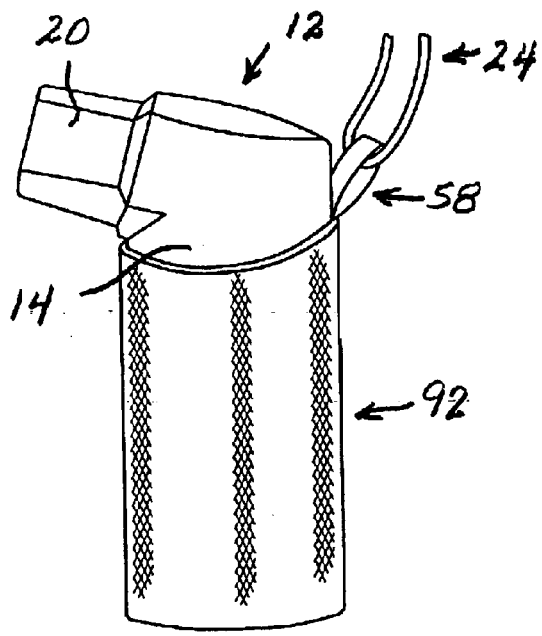
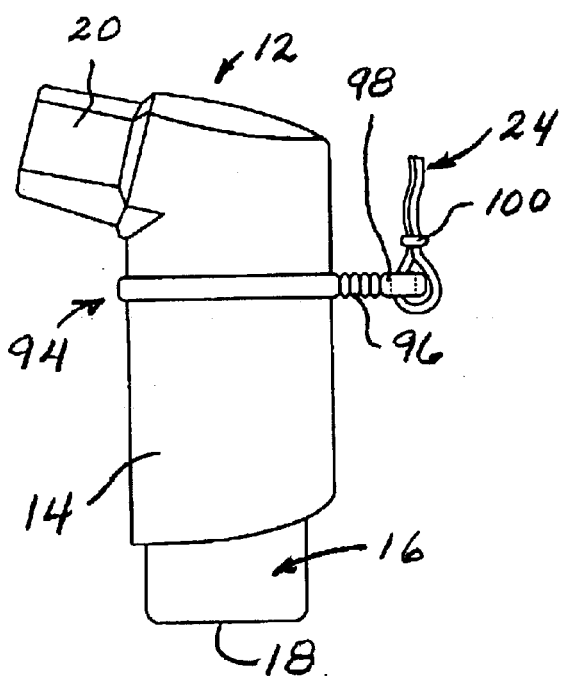

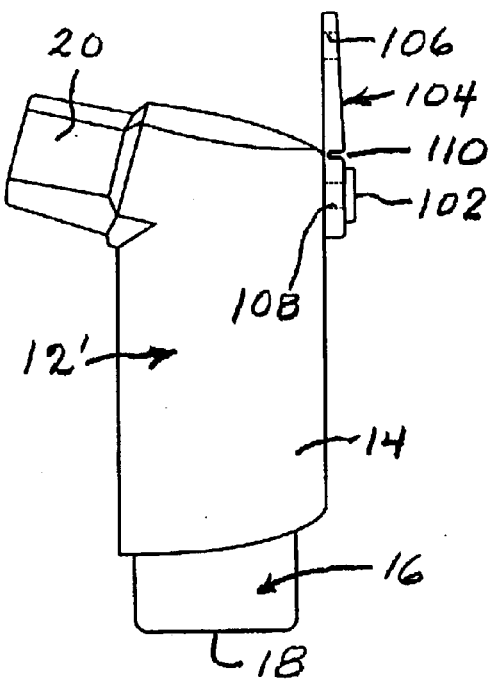
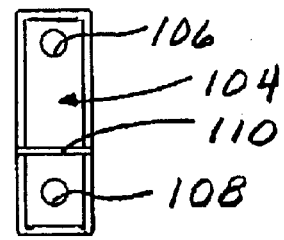
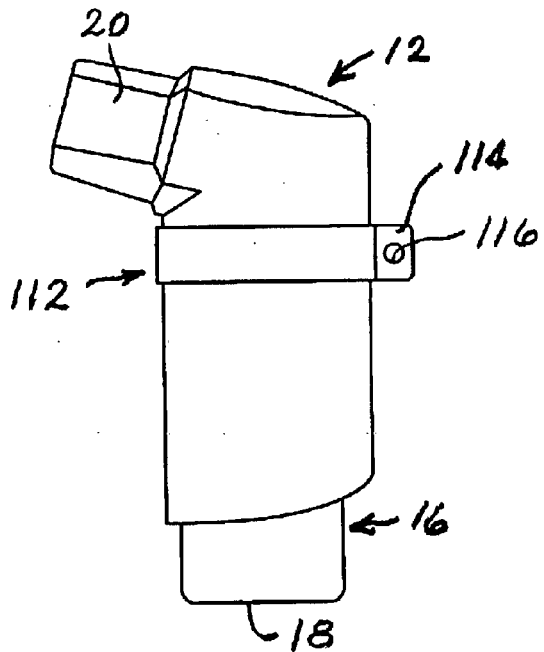
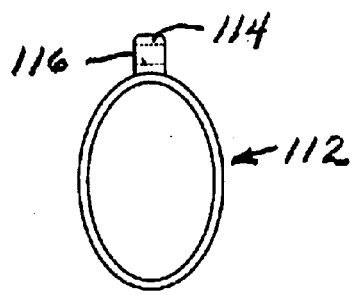
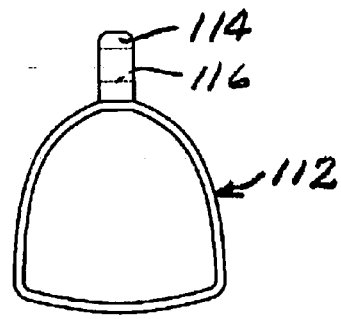

SUSPENDED INHALER RETAINER

The present application claims the benefit of the priority of Provisional Application Ser. No. 60/349,474 filed Jan. 18, 2002.

BACKGROUND OF THE INVENTION

1. Field of the Invention

The present invention relates to a comfortable, noncumbersome system for keeping a medication inhaler immediately accessible for use.

2. Description of the Prior Art

There are a wide variety of different medical conditions which require people to administer medication by inhalation. For example, asthmatic conditions, allergies, bronchial conditions, and other medical conditions and diseases require patients to employ medications that are inhaled. Such medications are often packaged in small, generally cylindrical, pressurized metal canisters, typically about one inch in diameter and about two inches in length. The medication canister has a medication dispensing end at which a valve is located, and an opposite, closed end. To extract medication from the canister a medication inhaler is required. A medication inhaler is constructed with a hollow body open at one end and having a generally cylindrical cavity to receive the canister therein.

The medical conditions that require the administration of medication by inhalation are often typified by lengthy dormant periods, punctuated by sudden onsets of attacks which leave the patient gasping for breath. For patients with such conditions it is extremely important for the medication inhaler to be readily at hand so that medication can be administered at once in the event of such an attack. To utilize the medication inhaler in which the medication is carried, the user places the mouthpiece between his or her lips and presses the medication inhaler. Pressing the inhaler ejects a measured amount of medication in a fine mist from the pressurized container which the user then inhales deeply into the bronchial passages. If medication is administered immediately in this manner, the sudden attack will usually quickly subside. However, rapid administration of the medication is extremely important in order to deal with such an attack. Therefore, patients who suffer from conditions such as an asthma, allergies, and other medical conditions requiring the use of inhalers must be ever vigilant so as to have their medication inhaler readily at hand.

Because long periods may elapse between attacks, a patient is quite likely to forget to transfer an inhaler with its medication canister from one set of clothing to another or from one purse to another. Also, even if a person has remembered to carry the medication inhaler in a pocket or in a purse, it still may be difficult to reach at the onset of an attack. For example, if the patient experiences an attack while driving or riding in a vehicle, it may be quite difficult and time-consuming to extract the medication inhaler from a pocket or purse. Consequently, the problem of immediate inhalation medication accessibility has plagued sufferers of bronchial conditions for years.

SUMMARY OF THE INVENTION

The present invention provides a unique, but simple and very expedient solution to the problem of immediate accessibility of inhalation medication. According to the present invention a medication inhaler is provided with a lanyard that is formed into a wearer neck encircling loop that is placed over the wearer's head and worn about the neck. This system allows the medication inhaler to hang suspended from the user's neck. A releasable coupling is provided that is positioned either within the lanyard or between the lanyard and the medication inhaler. The releasable coupling includes mutually engageable and separable coupling members that are normally maintained in a condition coupled together, but which will separate when a sufficient force is exerted tending to pull the medication inhaler away from the wearer's neck. The provision of such a releasable coupling is a safety feature that prevents injury to the user in the event that the medication inhaler becomes snagged on some object, such as a machine, a drawer pull, a doorknob, or some other object. Preferably the releasable coupling is positioned in the lanyard so that, if the lanyard itself becomes snagged, the coupling members will separate so that the lanyard cannot choke the wearer.

In one broad aspect the present invention may be considered to be an apparatus for carrying a medication inhaler comprising: a socket configured to receive and grip the medication inhaler; a lanyard secured to the socket and formed into a wearer neck loop; and a releasable coupling joined to the wearer neck loop and employing mutually engageable and separable coupling members that separate from each other when a predetermined force of separation is exerted on the coupling members. Preferably, the releasable coupling is constructed so that the coupling members will separate when opposing forces of between about one and about five pounds are exerted on them.

In another broad aspect the invention may be considered to be a combination of a medication inhaler having a hollow body, a lanyard formed into a wearer neck encircling loop and attached to the medication inhaler, and a releasable coupling joined to the lanyard and including mutually engageable and separable coupling members that separate from each other when a predetermined threshold of force is exerted on them from opposite directions. As previously stated, this threshold force is preferably in a range of from between about one and five pounds.

One preferred embodiment of the invention is a carrier for a medication container comprising: a sleeve for receiving and gripping the medication container therewithin; a flexible cord having opposing ends and formed into a loop and secured to the sleeve; and a releasable coupler including a pair of engageable and separable coupling members with longitudinally aligned, mutually interengageable elements that are detachable and engageable with each other and which are separable from each other by opposing longitudinal forces applied to the coupling members, and one of the engageable and separable coupling members is attached to each of the opposing ends of the flexible cord.

In another aspect the invention may be considered to be a method for a patient to carry a medication inhaler in an immediately accessible fashion utilizing a device configured to receive and grip the medication inhaler, a lanyard secured to the device and forming a wearer neck encircling loop, and a releasable coupling employing mutually engageable and separable coupling members, wherein at least one of the coupling members is attached to the lanyard, the steps comprising: engaging the separable coupling members together; inserting the medication inhaler into the socket; and placing the wearer neck encircling loop of the lanyard about a patient's neck, whereby the medication inhaler is suspended from the patient's neck by the lanyard.

The invention may be described with greater clarity and particularity by reference to the accompanying drawings.

DESCRIPTION OF THE DRAWINGS

FIG. 2 illustrates one alternative embodiment of the invention.

FIG. 2A illustrates a variation of the embodiment of the invention shown in FIG. 2.

FIG. 3 illustrates another alternative embodiment of the invention.

FIG. 3A is a plan detail illustrating the frame employed in the embodiment of FIG. 3 prior to folding.

FIG. 4 illustrates another alternative embodiment of the invention to that shown in FIG. 3.

FIG. 4A is a plan detail illustrating the frame employed in the embodiment of FIG. 4 prior to folding.

FIG. 5 illustrates another alternative embodiment of the invention.

FIG. 6 illustrates still another alternative embodiment of the invention.

FIG. 7 illustrates yet another alternative embodiment of the invention.

FIG. 7A is a plan detail illustrating the attachment link employed in the embodiment of FIG. 7 in isolation.

FIG. 8 illustrates another alternative embodiment of the invention.

FIG. 8A is a plan detail illustrating how the inhaler encircling loop of flexible material is resiliently deformed to encircle an inhaler having one body configuration in the embodiment of the invention shown in FIG. 8.

FIG. 8B is a plan detail illustrating how the inhaler encircling loop of flexible material is resiliently deformed to encircle an inhaler having another body configuration in the embodiment of the invention shown in FIG. 8.

DESCRIPTION OF THE EMBODIMENT AND IMPLEMENTATION OF THE METHOD

Figure 1:
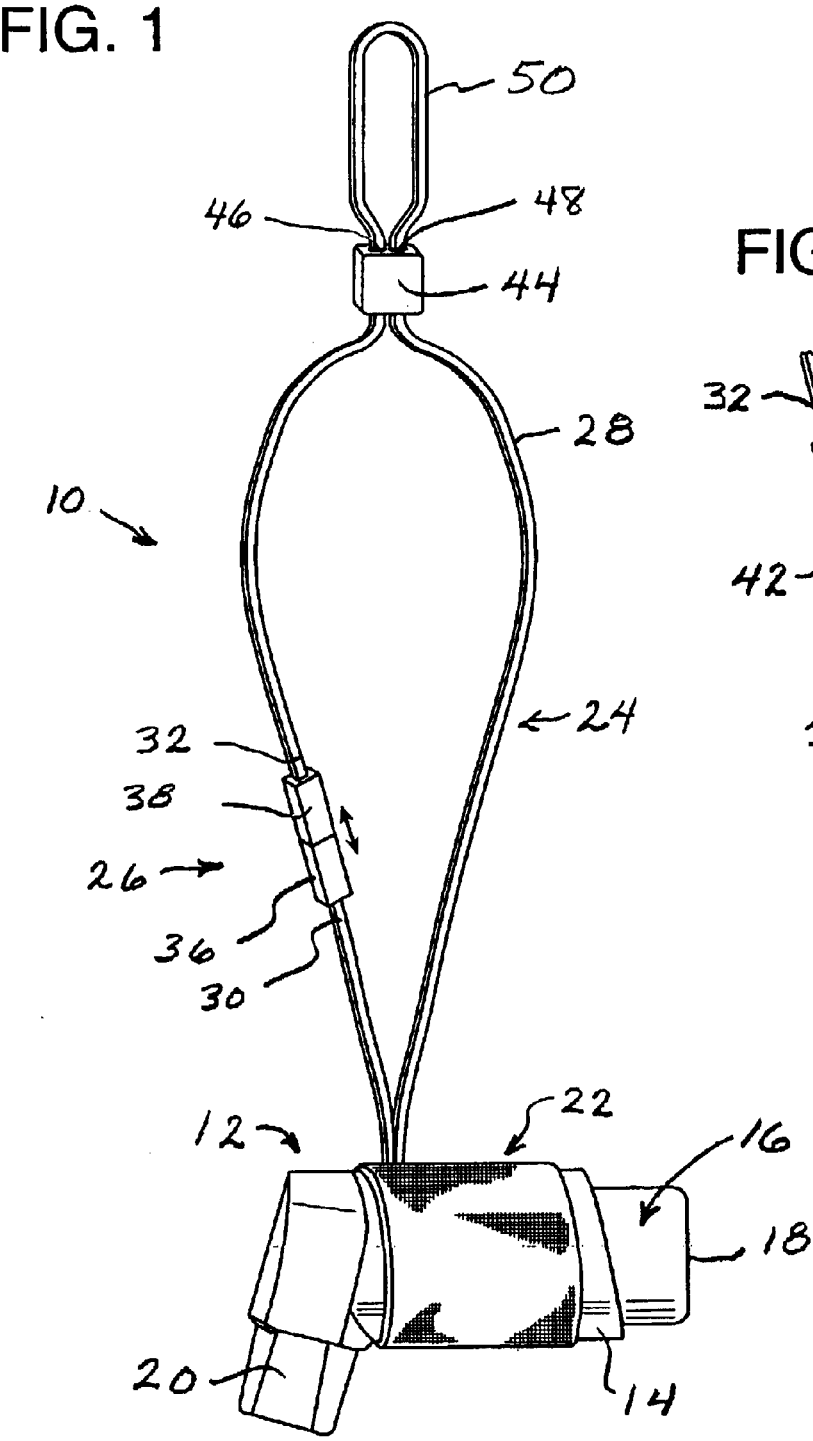
FIG. 1 is an elevational view illustrating one preferred embodiment of the invention.

FIG. 1 illustrates an apparatus indicated generally at 10 for carrying a medication inhaler 12. The medication inhaler 12 is a conventional medication inhaler having a hollow tubular body 14 having a generally cylindrical cavity defined therewithin to receive a conventional cylindrical inhalation medicament canister 16. The medicament canister 16 is of the conventional type that has a medication dispensing end that is not visible in FIG. 1, since it is inserted into the medication inhaler 12, and an opposite, closed end 18. The bottom end of the medication inhaler body 14 is open, and the closed end 18 of the medicament canister 16 is visible in FIG. 1 protruding therefrom.

The other end of the body 14 of the medication inhaler 12 is equipped with a conventional mouthpiece 20 which the patient inserts between his or her lips in order to receive medication out of the medicament canister 16. To obtain medication the patient places the mouthpiece in his or her mouth and presses the medication canister 16 further into the body 14 of the medication inhaler 12. This movement actuates a valve on the canister 16 that dispenses an aliquot portion of the medication as an aerosol spray through the mouthpiece 20. The patient inhales this spray through the mouth as deeply into the bronchial system as possible. It is often necessary to dispense several aliquot portions of the medication and inhale them in this manner before the attack will subside.

The outer surface configuration of the medication inhaler body 14 varies considerably with different manufacturers. For example, the outer surface configuration of the inhaler body 14 may be cylindrical, it may have an oval-shaped cross section, or it may have a polygonal outer cross-sectional shape. Medication inhalers 12 come in a variety of sizes and shapes from different manufacturers. However, both the medication inhaler 12 and the medicament canister 16 that is inserted into it are conventional, and need not be described in great detail.

The carrying apparatus 10 of the invention in the embodiment shown in FIG. 1 is comprised of a socket 22 configured to receive and grip the body 14 of the medication inhaler 12, a lanyard 24, and a releasable coupling 26. The lanyard 24 is formed into a wearer neck loop 28 and may be an elongated cord, leather thong, a ribbon, or any other type of line. The material of which the lanyard 24 is constructed is flexible, but may be either elastic or inelastic. As illustrated in FIG. 1, the lanyard 24 has opposing ends 30 and 32 to which a pair of mating, mutually engageable and separable male and female coupling members 36 and 38 are respectively attached. That is, one of the coupling members 36 and 38 is attached to each of the lanyard ends 30 and 32.

Figure 1A:
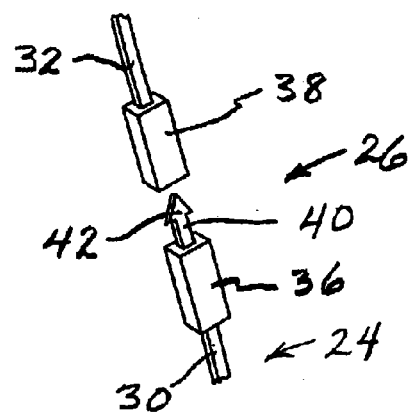
FIG. 1A is an exploded detail illustrating the manner of separation of the mutually engageable and separable coupling members employed in the embodiment of FIG. 1.

As shown in FIG. 1A the mutually engageable and separable coupling members 36 and 38 of the releasable coupling 26 will become detached from each other if a predetermined force of separation is exerted in opposite directions upon them. The preferred threshold force of separation is preferably between about one and about five pounds. The male coupling member 36 has a protruding stud 40 with an enlarged, arrow-shaped tip 42 that fits into a mating detent cavity defined within the hollow structure of the female coupling member 38. The hollow cavity within the coupling member 38 is formed with a reduced neck proximate the open end of the coupling member 38. The coupling members 36 and 38 may be formed of plastic or any other material that is sufficiently resilient to be elastically deformed to an extent sufficient to permit the enlarged tip 42 of stud 40 to pass through the reduced neck of the cavity defined within the mating coupling member 38.

The socket 22 illustrated in the embodiment of FIG. 1 is preferably formed as a sleeve from some elastomeric material, such as neoprene so that it will accommodate medication inhalers 12 having different body configurations and sizes. If the socket 22 is formed of an elastomeric material, such as neoprene, it forms a socket sleeve that has a girth that expands to receive the elongated body 14 of the medication inhaler 12, and retracts to snugly secure the medication inhaler 12 within its confines. The sleeve may be formed as a cylindrical tube from a rectangular strip of material, the ends of which are sewn together at an intermediate location to create the cylindrical sleeve. The lanyard 24 is folded back upon itself and sewn into the longitudinal seam formed in the socket 22 where the ends of the strip of material are sewn together to create a sleeve-like jacket about the inhaler 12. However, the lanyard 24 may be attached to the socket 22 by other types of fastening systems, some of which are hereinafter described.

The sleeve formed by the socket 22 may have a cylindrical shape in its undistended condition, if formed from a rectangular strip of neoprene as described above. Alternatively, the socket 22 may be formed from a trapezoidal-shaped strip of material, the ends of which are brought together and joined in longitudinal seam. With such a construction the sleeve formed by the socket 22 has a frusto-conical shape in which the diameter of the opening at one and is slightly larger than the opening at the other. This may be desirable to facilitate insertion of the body 14 of the medication inhaler 12 into the socket 22. The socket 22 may have many other variations in shape as well.

The carrier apparatus 10 illustrated in FIG. 1 is also provided with a wearer neck loop length adjustment slide 44 with at least one longitudinal opening defined therethrough. Preferably, the adjustment slide 44 is provided with a pair of parallel, cylindrical openings 46 and 48 defined through its structure. A portion of the wearer neck loop 28 of the lanyard 24 remote from the sleeve formed by the socket 22 passes through the wearer neck loop length adjustment slide 44. In the embodiment illustrated in FIG. 1 this is accomplished by stringing the lanyard 24 first through one of the openings 46 in one direction, and then back through the other opening 48 in the opposite direction before both of the coupling members 36 and 38 are attached to their respective ends 30 and 32 of the lanyard 24. The portion of the lanyard 24 on the side of the slide 44 remote from the socket 22 forms an adjustment loop 50. The separation between the wearer neck loop length adjustment slide 44 and the socket 22 is adjustable by moving the wearer neck loop length adjustment slide 44 along the wearer neck loop 28 to increase or decrease the circumference of the wearer neck loop 28, as desired by the wearer.

As is evident from FIG. 1, the patient requiring a medication inhaler 12 may insert his or her head through the wearer neck loop 28 so as to allow the inhaler 12 to hang by the lanyard 24 suspended within the socket 22 from the wearer's neck. Typically the overall length of the wearer neck loop 28, that is its circumference, is between about two and a half feet and five feet, depending upon the preference of the patient.

Some users will prefer for the socket 22 to be suspended right below the neck, in which case the wearer neck loop length adjustment slide 44 is moved closer to the socket 22. Other users will prefer a much longer wearer neck loop so that the socket 22 will hang much lower down on the wearer's torso. In this case the wearer neck loop length adjustment slide 44 is pushed quite far away from the socket 22 so that the adjustment loop 50 is extremely small. If the wearer neck loop length adjustment slide 44 is formed with a pair of holes 46 and 48, rather than a single hole, the slide 44 cannot be inadvertently pulled entirely off of the lanyard 24.

As is evident from FIGS. 1 and 1A, the releasable coupling 26 serves as a safety device. That is, if either the inhaler 12 or the wearer neck loop 28 becomes snagged on some object, such as a drawer pull, a doorknob, a corner of a desk, or any other object, the wearer will not be injured since the coupling members 36 and 38 will releasably separate from each other as illustrated in FIG. 1A. Furthermore, should this occur, the carrier 10 is not damaged in any way, since the stud 40 of the coupling members 36 can be reinserted into the detent cavity formed in the coupling member 38 to once again reengage the coupling members 36 and 38 with each other, thereby again closing the wearer neck encircling loop 28.

FIG. 2 illustrates one alternative embodiment of the invention employing a socket 52 in place of the socket 22. The socket 52 is not formed as a closed tubular structure, but rather as a band or strip of material having mutually engageable ends 54 and 56 with interengageable fasteners thereon. For example, the overlying ends 54 and 56 may be fastened together by a flexible, hook and loop fabric fastening system of the type sold under the registered trademark Velcro®. That is, the outwardly facing surface of the end of 54 may be equipped with a resilient, fabric matted pile, while the inwardly facing surface of the end 56 may bear a multiplicity of minute, flexible fabric hooks. The outer end 56 of the fabric band may be wrapped tightly about the inner end 54 in overlapping fashion to provide the sleeve formed by the socket 52 with an adjustable girth to accommodate conventional inhalers 12 of different sizes and configurations.

The extent of overlap between the band ends 54 and 56 may vary, depending upon the circumference of the body 14 of the medication inhaler 12. It is to be understood that different fastening systems may be substituted for the Velcro® fastening arrangement described. For example, the ends 54 and 56 of the encircling band forming the socket 52 may be releasably coupled together by snap fasteners or other conventional fastening devices.

The fabric socket 52 illustrated in the embodiment of FIG. 2 is secured to the lanyard 24 by a releasable coupling device 57 that includes mutually engageable and separable coupling members 62 and 66. The coupling members 62 and 66 are releasably detachable from each other when a force of separation of between about one and about five pounds is exerted tending to pull the socket 52 away from the lanyard 24.

The socket 52 is provided with an eyelet 58, which may be a short length of ribbon or fabric threaded through an aperture 60 in the coupling member 62. This length of material is then doubled over and its ends are sewn together along one edge of the band of material forming the socket 52 to create the eyelet 58. The lanyard 24 is threaded through another opening 64 in the mating coupling member 66. The coupling 57 thereby joins the lanyard 24 to the socket 52. The coupling member 62 is anchored to the eyelet 58 while the other coupling member 66 is anchored to the lanyard 24.

Should the inhaler 12 snag or catch in an office machine the releasable coupling members 62 and 66 of the coupler 57 will separate from each other, thereby protecting the neck of the user from injury due to force on the lanyard 24. The coupler 57 may be supplied in addition to or in place of the coupler 26 in the lanyard 24.

FIG. 2A shows a variation of the system illustrated in FIG. 2. In the system of FIG. 2A a swivel clip 70 is formed with a hook that releasably engages the eyelet 58. The opening of the hook is closed by a spring loaded catch. At its base, the swivel clip 70 has a swivel connector 72 to which a fastening ring 74 is attached. The lanyard 24 is threaded through the fastening eye formed in the fastening ring 74. Since the system illustrated in FIG. 2A does not employ a releasable coupler between the lanyard 24 and the socket 52, it must be provided with a coupling system, such as the coupler 26 in the wearer neck loop 28 so as to prevent injury to a user.

FIG. 3 and FIG. 3A illustrate another embodiment of the invention that utilizes a socket 76 formed from a sheet of material 78, illustrated in plan view prior to folding in drawing FIG. 3A. The sheet of material 78 is shaped generally as a figure eight with a fastening tab 80 at one end. The sheet of material 78 thereby forms a frame with a pair of rings 81 and 83 having inhaler receiving openings 82 and 84 of equal cross section defined respectively therethrough. The fastening tab 80 has a lanyard engaging aperture 86 defined therethrough.

The sheet of material 78 is folded essentially in half, bringing the ring 81 on top of the ring 83 so that the inhaler receiving openings 82 and 84 are in substantially coaxial alignment. The inhaler 12 is inserted through both of the inhaler receiving openings 82 and 84, as illustrated in FIG. 3. The lanyard 24 is threaded through the opening 86 and is thereby attached to the fastening tab 80. The folded structure of the frame 78 thereby forms a socket that receives the inhaler 12. The weight of the inhaler 12 tends to pull up on the fastening tab 80 thereby tilting the frame rings 81 and 83 out of precise coaxial alignment. This causes the frame 78 to grip the outer surface of the body 14 of the inhaler 12.

FIGS. 4 and 4A illustrate a modification of the system shown in FIGS. 3 and 3A. The socket 90 illustrated in FIG. 4 is also formed with a frame 78 configured in the shape of a figure eight. The frame 78 includes a pair of ring-shaped portions 81 and 83 through which inhaler receiving openings 82 and 84 are respectively defined. A fastening tab 88 is located at the intersection of the ring-shaped portions 81 and 83 and projects outwardly perpendicular to the plane of the frame 78 when the frame 78 is in an unfolded condition, as illustrated in FIG. 4A. The fastening tab has a fastening aperture or eye 91 defined therethrough.

To form the socket 90, the frame 78 is folded in half between the inhaler receiving openings 82 and 84 so that the inhaler receiving openings 82 and 84 are coaxially aligned with each other and the fastening tab 88 projects laterally outwardly from the intersection of the rings 81 and 83, as illustrated in FIG. 4. The inhaler 12 is then inserted through both of the inhaler receiving openings 82 and 84 so that the fastening tab 88 projects outwardly from the inhaler 12. The lanyard 24 is threaded through the fastening eye 91 so that it is attached to the fastening tab 88.

The resiliency of the sheet of material forming the frame 78 is such that the edges of the rings 81 and 83 of the frame 78 are slightly biased apart, thus tending to force the inhaler receiving openings 82 and 84 out of precise coaxial alignment. This divergence of the orientation of the rings 81 and 83 thereby causes the socket 90 to grip the outer surface of the inhaler 12. The inhaler 12 then hangs suspended from the lanyard 24, which is worn about the neck of a wearer. The inhaler 12 is captured by the socket 90 within the confines of the inhaler receiving openings 82 and 84 of the frame 78.

FIG. 5 illustrates still another embodiment of the invention employing a socket 92 that it is formed of a flexible, elastomeric material, such as neoprene, in the shape of a cup. The cup-shaped socket 92 has an open mouth at its upper end and a closed floor at its bottom. The upright side walls of the socket 92 surround the body 14 of the inhaler 12 and the floor of the socket 92 supports the inhaler 12 from its lower end. The flexible bottom of the cup allows a user to depress the canister 16 deeper into the body 14 of the inhaler 12. Also, since the socket 92 is formed of a flexible, elastically resilient material, the upright side walls of the socket 92 conform to the shape of the inhaler 12. The socket 92 is thereby able to firmly grip a variety of different inhalers 12, the shapes of the bodies 14 of which vary from one manufacturer to another.

Like the socket 52, the socket 92 is provided with a fastening eyelet 58 formed of a short strip of cloth, ribbon, or some other material that can be formed into a small loop. The eyelet 58 forms a lanyard attachment loop that projects upwardly from the open mouth of the socket 92. The lanyard 24 is threaded through the eyelet 58 so that the inhaler 12 hangs suspended from the lanyard 12 about the neck of a wearer. The lanyard is secured to the lanyard attachment loop by treading one of the lanyard ends 30 or 32 through the eyelet 58 before securing the releasable coupling members 36 and 38 together.

FIG. 6 illustrate another alternative embodiment of an inhaler carrier according to the invention. In this embodiment the socket 94 is formed as a laterally encircling ring having an adjustable girth. The ring-shaped socket 94 is provided with a knurled girth adjustment slide 96 having a central, axial opening therethrough. A portion of the ring-shaped socket is pinched together and inserted through the central opening in the girth adjustment slide 96 and pulled through to the other side to form a separate lanyard—attachment loop 98 that is considerably smaller than the portion of the socket 94 encircling the inhaler 12. The lanyard 24 is routed through the opening of the lanyard attachment loop 98. If desired, a slip ring 100 may be utilized on the lanyard 24 to tighten the bight of the lanyard 24 on the lanyard attachment loop 98. The inhaler 12 can then hang suspended about the neck of the wearer from the lanyard 24, as with the other embodiments of the invention described.

FIG. 7 illustrates a further embodiment of the invention suitable for use with some models of inhalers, specifically those models that have studs projecting from them opposite the mouthpiece 20. As illustrated in FIG. 7, the inhaler at 12' is provided with a small, button-shaped stud 102 that projects laterally outwardly from its backside at a location opposite the mouthpiece 20. An attachment link 104 is provided and is illustrated in isolation in FIG. 7A.

The attachment link 104 has opposing ends and is provided with a lanyard aperture 106 at one end and an inhaler stud aperture 108 at the other of its op posing ends. The attachment link 104 is formed of a resilient plastic material with a transverse crease 110 across one side of its structure located between its opposing ends. The crease 110 in the attachment link 104 facilitates manual manipulation of the inhaler 12'.

To utilize the device, the lanyard 24 is strung through the lanyard aperture 106 and the attachment link 104 is pressed onto the stud 102 which is engaged within the stud attachment aperture 108 by a frictional force. The attachment link 104 thereby fits over and releasably grips the stud 102 projecting from the medication inhaler 12', as illustrated in FIG. 7.

FIGS. 8, 8A, and 8B illustrate another embodiment of the inhaler carrying apparatus of the invention. In this embodiment the socket 112 is constructed of a resilient, flexible material in the shape of a closed, annular, encircling loop, as illustrated in FIG. 8A. The socket 112 has an outwardly projecting tab 114 with a lanyard attachment aperture 116 defined therethrough. The encircling loop-shaped socket 112 is preferable formed of an elastic material so that the size as well as the shape of the encircling loop can be changed to fit different inhalers 12. For example, the upper portions of the body 14 of some inhalers 12 are oval-shaped. The loop-shaped socket 112 will then have the configuration illustrated in FIG. 8A when placed about inhalers 12 of this type in the manner illustrated in FIG. 8.

However, since the loop-shaped socket 112 is elastic and flexible it may be elastically distended into other configurations, as illustrated in FIG. 8B so as to encircle and snugly grip the upper portions of bodies 14 of inhalers 12 having odd sizes and shapes. In its undistended state the elastic loop-shaped socket 112 forms an enclosing loop small enough to pass about and snugly grip commercially available inhalers 12 of relatively small size. On the other hand, the loop formed by the loop-shaped socket 112 can be stretched to enlarge the loop opening to fit about and grip the bodies 14 of inhalers 12 of larger sizes.

Figure 9:
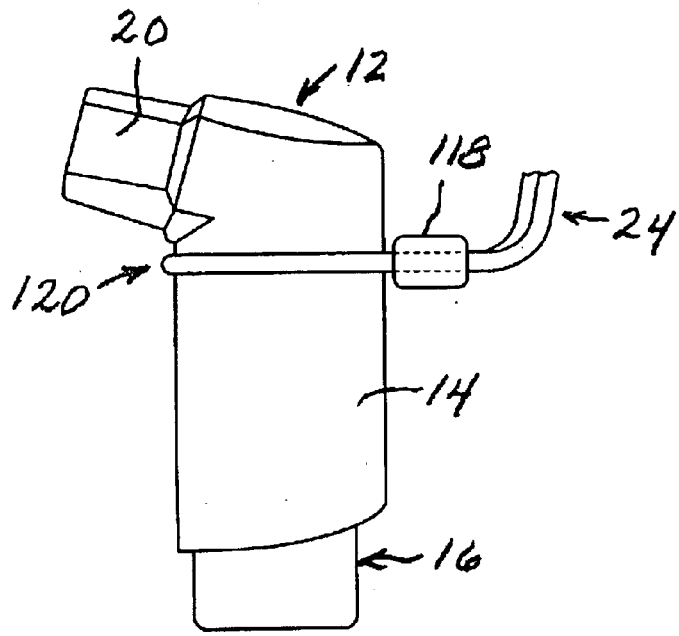
FIG. 9 illustrates another alternative embodiment of the invention.

FIG. 9 illustrates another alternative embodiment of the invention which does not require a socket separate from the lanyard 24. Rather, the lanyard 24 is provided with a cinch slide 118 having a central opening therethrough. A portion of the lanyard 24 is bent back upon itself and inserted through the central, axial opening of the cinch slide 118 to form an inhaler encircling loop 120. The cinch slide 118 delineates the inhaler encircling loop 120 from the wearer neck encircling loop 28. The cinch slide 118 is pressed toward the body 14 of the inhaler 12 so that a portion of the lanyard 24 itself encircles and grips the inhaler 12. A separate socket is therefore not required. In a slight modification of this system the cinch slide 118 may be provided with a pair of mutually parallel but separate apertures defined therethrough, and the lanyard 24 may be threaded through these apertures to form the inhaler circling loop 120.

Figure 9A:
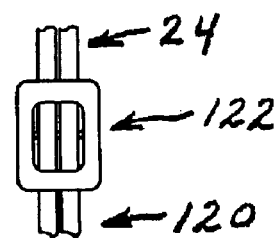
FIG. 9A is a plan detail showing an alternative slide that may be employed in place of that illustrated in FIG. 9.

FIG. 9A illustrates a modification of this system in which a slide buckle 122 is substituted for the cinch slide 118. The slide buckle 122 is formed as a rectangular-shaped ring with transverse end bars at its opposing longitudinal ends and a transverse crossbar extending across its center. The inhaler encircling loop 120 is threaded beneath one transverse end bar of the cinch buckle 122, up and over the central crossbar and back down beneath the opposite end bar of the cinch buckle 122. The cinch buckle 122 shown in FIG. 9A operates in the same manner as the cinch slide 118 illustrated in FIG. 9.

Figure 10:
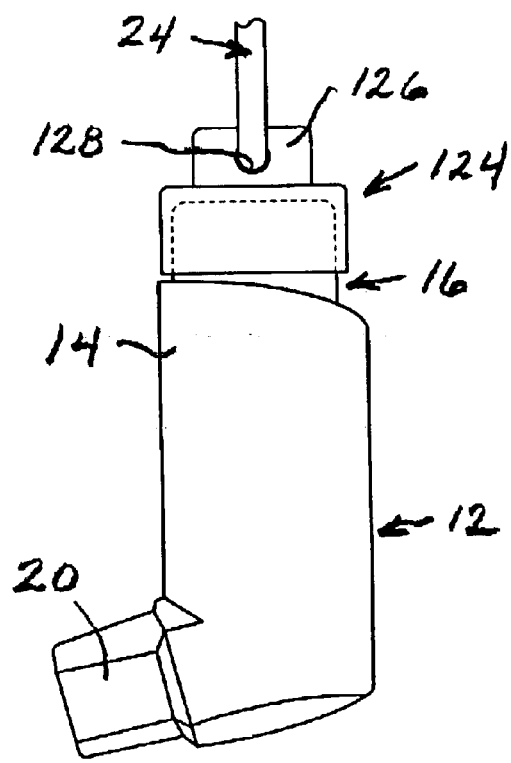
FIG. 10 illustrates another alternative embodiment of the invention.
Figure 10A:
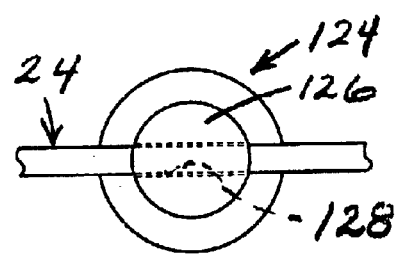
FIG. 10A is a top plan detail of the embodiment of FIG. 10.

FIGS. 10 and 10A illustrate another embodiment of the invention that does not require a separate socket. Rather, once the medication dispensing end of the medication canister 16 is inserted into the hollow body 14 of the medication inhaler 12, the opposite, closed end 18 of the medication canister 16 protrudes from and extends beyond the open end of the hollow inhaler body 14. A canister boot 124, preferably formed of a flexible, resilient, he elastic material such as neoprene, is provided. The canister boot 124 has a cylindrical annular wall configuration, and has an open mouth at one end. The opposite end of the boot 124 is closed and has a lanyard attachment knob 126 projecting from it in a direction opposite the open mouth of the cavity defined within the canister boot 124.

A transverse lanyard receiving tunnel 128 is defined through the structure of the lanyard attachment knob 126. The lanyard 24 is threaded through the tunnel 128 so that the inhaler 12 is normally held suspended in an inverted orientation as illustrated in FIG. 10. The lanyard 24 is secured to the canister boot 124 so that the medication canister 16 and the canister boot 124 couple the lanyard 24 to the medication inhaler 12.

Figure 11:
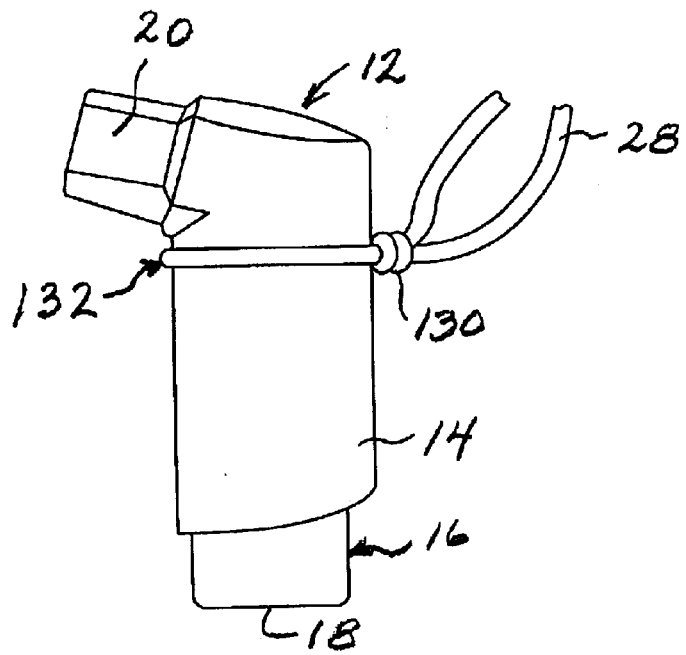
FIG. 11 illustrates another alternative embodiment of the invention.

FIG. 11 illustrates another embodiment of the invention which does not require a separate socket. In the embodiment illustrated in FIG. 11 a slipknot 130 is formed in the lanyard 24 to define an inhaler circumscribing loop 132 that is delineated from the wearer neck encircling loop 28 by the slipknot 130. The slipknot 130 is cinched tightly against the medication inhaler 12 to snugly capture it within the inhaler circumscribing loop 132.

Figure 12:
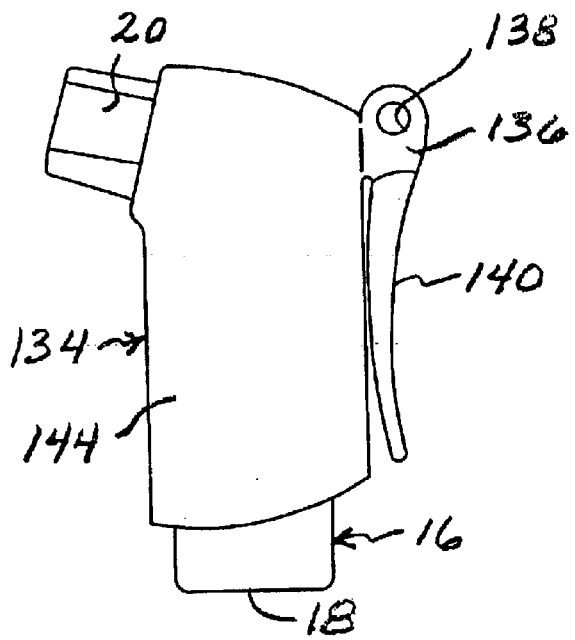
FIG. 12 illustrates still another alternative embodiment of the invention.
Figure 12A:
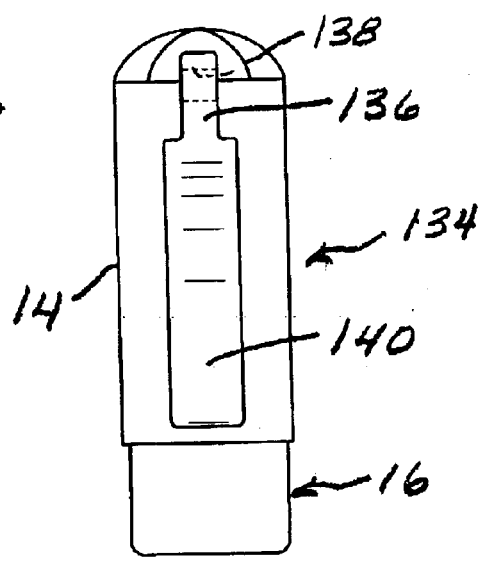
FIG. 12A is a side elevational view of the embodiment shown in FIG. 12.

FIGS. 12 and 12A illustrate still another embodiment of the invention in which medication inhaler 134 is specifically designed to be suspended from a lanyard, such as the lanyard 24. The medication inhaler 134 is provided with an attachment tab 134 that is integrally formed as a part of the inhaler body 144 and projects rearwardly from the upper end of the inhaler 134 opposite the mouthpiece 20. The lanyard 24 may be threaded through the fastening eye 138 in the lanyard attachment tab 136. The lanyard 24 is thereby secured to the inhaler 134 by means of the attachment tab 136.

The inhaler 134 accommodates a conventional medicament canister 16 within its hollow body. In the embodiment of the invention illustrated in FIGS. 12 and 12A, the inhaler 134 is also provided with an elongated, prong-shaped, resilient clip 140. The clip 40 is secured at one of its ends to the inhaler 134 by its connection to the attachment tab 136. The opposite, free end of the clip may be flexed to allow the inhaler 134 to be clipped to a belt, shirt pocket, or some other article of apparel worn by the user. By utilizing a clip such as the clip 140, the inhaler 134 does not dangle freely about the neck of the wearer, and thus will not swing about as the wearer moves.

Numerous other variations and modifications of the invention are also possible within the scope of the invention. One critical features of the invention resides in the provision of a flexible cord or lanyard for suspending a medication inhaler about the neck of the wearer so that the wearer always has the inhaler readily at hand. The other critical feature is that the neck cord or lanyard is provided with a releasable coupler having mutually engageable and releasable coupling elements or members that are normally joined together, but which may be pulled apart from each other by a relatively small force. The user is thus protected from injury or discomfort should the lanyard for the inhaler become snagged on some object. Other modifications and variations will become readily apparent to those familiar with the construction and use of medication inhalers. Accordingly, the scope of the invention should not be construed as limited to the specific embodiment depicted and described, but rather is defined in the claims appended hereto.

I claim:

1. An apparatus for carrying a medication inhaler comprising:

a socket configured to receive and grip said medication inhaler, a lanyard secured to said socket and formed into a wearer neck loop, and a releasable coupling joined to said wearer neck loop and employing mutually engageable and separable coupling members that separate from each other when a predetermined force of separation is exerted on said coupling members, wherein said socket is provided with an eyelet and one of said coupling members is anchored to said eyelet while the other of said coupling members is anchored to said lanyard.

2. An apparatus for carrying a medication inhaler comprising:

a socket configured to receive and grip said medication inhaler, a lanyard secured to said socket and formed into a wearer neck loop, and a releasable coupling joined to said wearer neck loop and employing mutually engageable and separable coupling members that separate from each other when a predetermined force of separation is exerted on said coupling members wherein said socket is formed from a sheet of material that defines a frame having a pair of inhaler receiving openings of equal cross section formed therethrough and a fastening tab with an aperture therethrough located between said inhaler receiving openings and said frame is folded between said inhaler receiving openings so that said inhaler receiving openings are aligned with each other and said inhaler is inserted through both of said inhaler receiving openings so that said fastening tab projects outwardly from said inhaler and said lanyard is attached to said fastening tab.

3. In combination, a medication inhaler having a hollow body, a lanyard formed into a wearer neck encircling loop, and attached to said medication inhaler, a releasable coupling joined to said lanyard and including mutually engageable and separable coupling members that separate from each other when a predetermined threshold force is exerted on them from opposite directions, and further characterized in that said medication inhaler has a stud projecting therefrom and further comprising an attachment link with opposing ends formed of a resilient material and said attachment link has a lanyard aperture at one of said opposing ends and said lanyard passes through said lanyard aperture, and said attachment link has an inhaler stud aperture at said other of its opposing ends for fitting over and releasably gripping said stud projecting from said medication inhaler.

4. In combination, a medication inhaler having a hollow body, a lanyard formed into a wearer neck encircling loop and attached to said medication inhaler;

a releasable coupling joined to said lanyard and including mutually engageable and separable coupling members that separate from each other when a predetermined threshold force is exerted on them from opposite directions, and wherein said medication inhaler is formed with an attachment tab through which a lanyard attachment aperture is defined, and said lanyard passes through said lanyard attachment tab to secure said lanyard to said medication inhaler.

* * * * *